United States Patent
Mielnik

(10) Patent No.: US 7,622,074 B2
(45) Date of Patent: Nov. 24, 2009

(54) INTEGRATED DECONTAMINATION/AERATION SYSTEM FOR VEHICLES

(75) Inventor: Thaddeus J. Mielnik, Concord, OH (US)

(73) Assignee: Steris Inc., Temecula, CA (US)

( * ) Notice: Subject to any disclaimer, the term of this patent is extended or adjusted under 35 U.S.C. 154(b) by 403 days.

(21) Appl. No.: 11/473,873

(22) Filed: Jun. 23, 2006

(65) Prior Publication Data

US 2006/0289490 A1 Dec. 28, 2006

Related U.S. Application Data

(60) Provisional application No. 60/694,513, filed on Jun. 28, 2005.

(51) Int. Cl.
*A61L 2/20* (2006.01)
(52) U.S. Cl. .................. 422/28; 422/33; 422/292; 422/300
(58) Field of Classification Search ............ 422/28, 422/33, 292, 300
See application file for complete search history.

(56) References Cited

U.S. PATENT DOCUMENTS

| | | | |
|---|---|---|---|
| 4,687,686 | A | 8/1987 | Stofleth et al. |
| H1197 | H | 6/1993 | Mank et al. |
| 5,327,744 | A | 7/1994 | Frawley et al. |
| 5,954,577 | A | 9/1999 | Meckler |
| 6,001,057 | A | 12/1999 | Bongiovanni et al. |
| 6,189,368 | B1 | 2/2001 | Ichida et al. |
| 6,402,812 | B1 | 6/2002 | Perrotta et al. |
| 6,692,694 | B1 | 2/2004 | Curry et al. |
| 6,734,405 | B2 | 5/2004 | Centanni et al. |
| 6,796,896 | B2 | 9/2004 | Laiti |
| 6,875,399 | B2 | 4/2005 | McVey |
| 2002/0098109 | A1* | 7/2002 | Nelson et al. ............ 422/5 |
| 2003/0138344 | A1 | 7/2003 | Mielnik et al. |
| 2004/0184950 | A1 | 9/2004 | McVey et al. |
| 2005/0013727 | A1 | 1/2005 | Hedman |
| 2005/0074359 | A1 | 4/2005 | Krieger |
| 2005/0175500 | A1* | 8/2005 | Adams et al. ............ 422/29 |

FOREIGN PATENT DOCUMENTS

| | | |
|---|---|---|
| DE | 11 78 550 | 9/1964 |
| EP | 1 226 834 | 7/2002 |
| GB | 2 250 200 | 6/1992 |

OTHER PUBLICATIONS

Definition of "integrate." The American Heritage@ Dictionary of the English Language, Fourth Edition. Houghton Mifflin Company, 2004. Answers.com Apr. 11, 2009. http://www.answers.com/topic/integrate.*

* cited by examiner

*Primary Examiner*—Sean E Conley
(74) *Attorney, Agent, or Firm*—Hudak, Shuk & Farine Co. LPA

(57) ABSTRACT

An integrated duct system is utilized to admit an antimicrobial vapor into a vehicle to decontaminate the contents and surfaces of the vehicle and subsequently to remove the vapor. The ducts comprise an air conditioning and/or heating duct, a decontamination duct for admitting an antimicrobial vapor, an auxiliary circulation duct for diffusing the vapor throughout the vehicle, and an aeration duct for removing the vapor from the vehicle, as well as a catalytic converter for detoxifying the antimicrobial vapor before removal. The integrated decontamination system is suitable for the chemical or biological decontamination of vehicles, provides enhanced vapor delivery and distribution on a rapid basis and also provides for rapid aeration for removing the antimicrobial vapor.

7 Claims, 1 Drawing Sheet

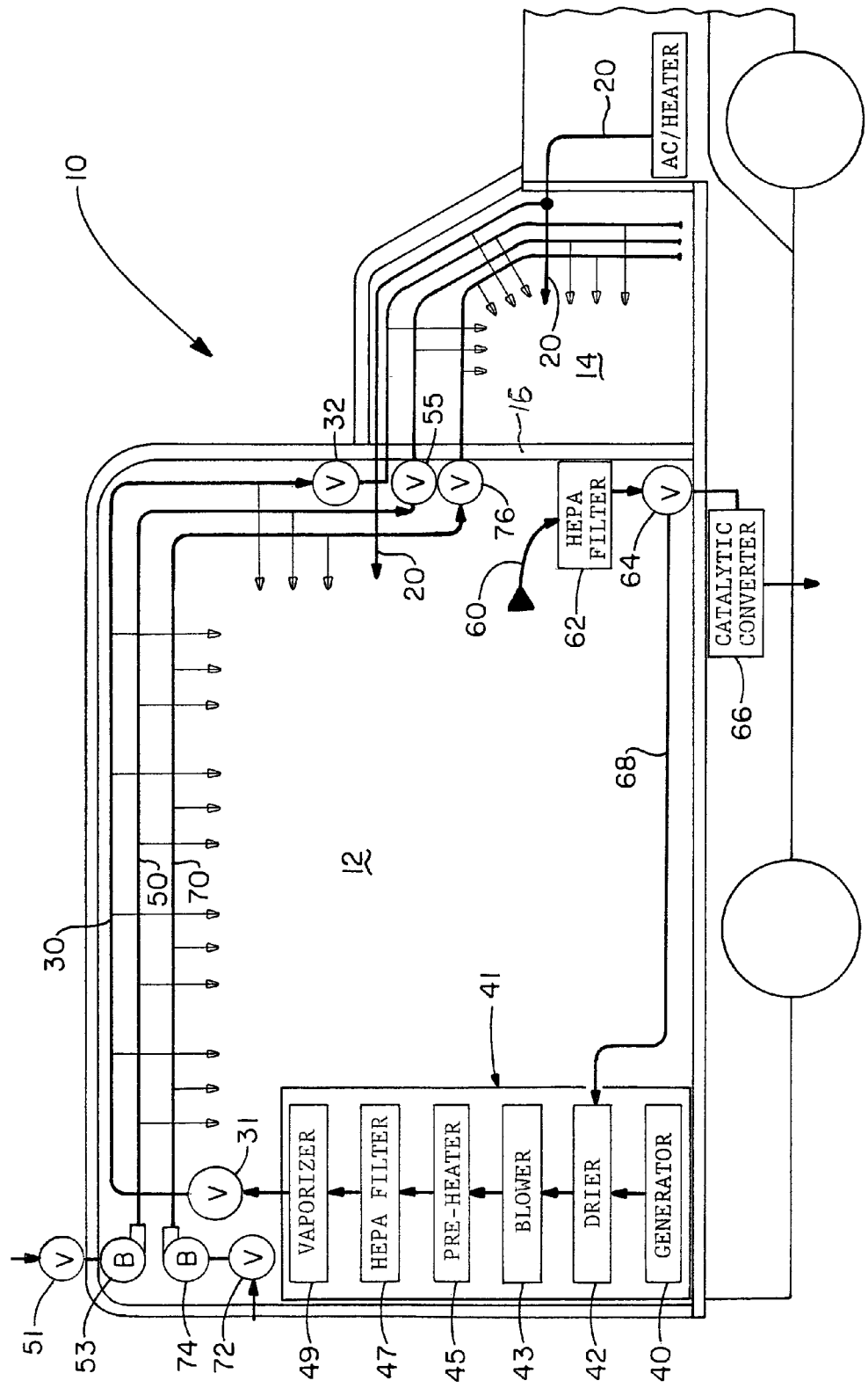

INTEGRATED DECONTAMINATION/AERATION SYSTEM FOR VEHICLES

CROSS-REFERENCE

This application claims the priority of U.S. Provisional Application Ser. No. 60/694,513, filed on Jun. 28, 2005, of Thaddeus J Mielnik, et al, for AN INTEGRATED DECONTAMINATION/AERATION SYSTEM FOR VEHICLES.

FIELD OF THE INVENTION

The invention relates to an integrated duct system to admit and diffuse an antimicrobial vapor into a vehicle in an effective and rapid manner (short cycle time) and to rapidly remove the vapor therefrom.

BACKGROUND OF THE INVENTION

Heretofore, decontamination of vehicles involved various methods such as vacuuming the floor of the vehicle and passing the removed air, dirt, debris, etc., through the filters so as to catch the particles and/or detoxify the same. Another commonly used method related to washing various portions of the vehicle such as with a bactericide to kill germs, and the like.

Such methods were not very effective inasmuch as they did not kill or detoxify various types of antimicrobial compounds, and that often various portions of the vehicle were simply not treated.

U.S. Publication No. 2003/0138344, published Jul. 24, 2003, relates to a system for handling mail in the form of a modular facility, which is capable of being isolated from the surrounding environment. The modular facility includes an enclosure or sorting area for receiving and sorting incoming mail. A decontamination system receives sorted mail and decontaminates the mail with an antimicrobial gas, such as ethylene oxide. A clean room, isolated from the enclosure and spaced from the enclosure by the decontamination system, is used for receiving processed mail from the decontamination system and sorting the mail for distribution. A source of a decontaminant gas, such as vapor hydrogen peroxide, is fluidly connected with the enclosure for supplying the decontaminant gas to the enclosure in the event that the sorting room is contaminated or suspected of being contaminated with a pathogenic biological or chemical agent.

U.S. Publication No. 2004/0184950, published Sep. 23, 2004, relates to when microbial contamination is introduced into a room of an enclosure, such as a building, an HVAC system including supply ductwork and a return ductwork is decontaminated with hydrogen peroxide vapor. A decontamination controller operates controllable baffles at outlet registers, temporary controllable baffles at inlet registers, and a blower system to circulate hydrogen peroxide vapor from hydrogen peroxide vapor generators through the ductwork in both forward and reverse directions. Further, at least portions of the baffles are closed to create dwell times in which the hydrogen peroxide vapor resides in the ductwork with minimal or turbulent flow.

SUMMARY OF THE INVENTION

In accordance with one aspect of the invention, an integrated duct system is provided for decontaminating a vehicle. A decontamination duct supplies an antimicrobial vapor to the vehicle to decontaminate various microorganisms within the vehicle. In order to increase the rate of destruction of the microorganisms, an auxiliary circulation duct is provided which can supply quantities of a gas such as air to rapidly diffuse the antimicrobial vapor and generate sufficient turbulence, etc., so that the vapor reaches and contacts all contents, items and surfaces within the vehicle. In one embodiment, a catalytic converter is utilized to detoxify the microbial vapor, for example vapor hydrogen peroxide (VHP) into water and oxygen. An aeration duct is also provided to provide a gas such as air to purge the vehicle of the antimicrobial vapor and reduce the level of any remaining vapor within the vehicle to a low and safe amount.

In accordance with another aspect of the present invention, a method of decontaminating a vehicle is provided. Steps of the method comprise providing the vehicle with a decontamination duct and admitting an antimicrobial vapor through the duct into the vehicle. The vehicle is also provided with an auxiliary circulation duct for admitting a gas into the vehicle to diffuse the antimicrobial vapor. The vehicle is also provided with an aeration duct for exhausting the non-reacted antimicrobial vapor from the vehicle. A catalytic converter is also provided for detoxifying the antimicrobial vapor before it is exhausted from the vehicle.

An advantage of the present invention is that the entire interior portion of the vehicle can be effectively treated with an antimicrobial vapor to decontaminate the same. Another advantage is that the vehicle can contain an antimicrobial generator such as a vapor hydrogen peroxide generator. Yet another advantage is that during the decontamination cycle, the antimicrobial vapor can be recycled through the vehicle to ensure coverage of all surfaces. Still another advantage is that the vehicle can be rapidly decontaminated and aerated.

BRIEF DESCRIPTION OF THE DRAWINGS

The single FIGURE is a diagrammatic illustration of a vehicle showing an integrated duct system utilized to admit an antimicrobial vapor as well as to remove the same.

DETAILED DESCRIPTION OF THE INVENTION

The vehicles which can be treated by the integrated duct system of the present invention include any vehicle which can be utilized to treat a patient and include emergency medical safety (EMS) vehicles including ambulances and patient transport vehicles; various types of military vehicles including transportation vehicles, emergency treatment vehicles, vehicle type hospitals, and the like; as well as various types of aircrafts.

Referring to the drawing, vehicle 10 contains patient transport area 12 and driver or cockpit area 14. The two areas are generally separated by a wall 16 which can have a door (not shown) therein to permit access from one area to the other.

The integrated duct system employs a plurality of integrated ducts to achieve a rapid decontamination of the vehicle. The presence of an air conditioning/heating duct 20 is optional but desired. Such air condition/heating duct is generally original equipment of the manufactured vehicle and the same duct network is known to the art and to the literature. The air within the vehicle such as the patient transport area desirably has low humidity in order to enhance the efficiency of the antimicrobial vapor. Thus, the air conditioner of the vehicle is generally initially utilized to reduce the humidity. Optionally, the temperature in the patient area can be increased by the heater. The exhaust portions of the air conditioning and/or heating ducts are generally located on the dashboard in cockpit area 14, and on the roof and/or side portions of the vehicle in patient transport area 12. The air conditioning/heating system is generally operated independently of the remaining duct networks.

An essential component of the present invention is the existence of decontamination duct network 30 which supplies the antimicrobial vapor to the interior of the vehicle. As with other duct networks such as auxiliary circulating duct network 50 and aerating duct network 70, each has a plurality of outlets located along the length of the network from the initial portion thereof to the end portion thereof. With respect to each duct network, a two-way valve is located in the vicinity of wall 16 which confines the item being transported to either patient transport area 12, or additionally to driver area 14. Each duct network can contain only one conduit or chamber generally along the length of the vehicle, or there can be branches off of the main conduit, or a multiplicity of conduits can exist such as two or three. The conduits can extend along the roof area of the vehicle, or the sidewalls thereof, or both.

Decontamination duct network 30 is provided or supplied with an antimicrobial vapor. An antimicrobial compound can be in the form of a liquid and can be stored in a container (not shown) within the vehicle and when needed is heated to generate a vapor. Alternatively and often desirably the vapor can be made by antimicrobial generator 40 also located within the vehicle. Such generators are known to the art as well as to the literature. The antimicrobial vapor which is used to decontaminate the patient area or the patient and the driver area of the vehicle comprise peroxy compounds such as peracetic acid, or preferably hydrogen peroxide, various aldehydes such as formaldehyde vapors, vapors of various phenols and derivatives thereof, and the like. Examples of specific phenols including catechol, resorcinol, and hydroquinone; alkyl dihydroxybenzenes; halogen substituted phenols, such as chlorophenols, alkyl and/or aromatic substituted chlorophenols; nitrophenols, dinitrophenols, trinitrophenols, and alkyl or aromatic substituted nitrophenols; aminophenols; aromatic, alkyl aromatic, and aromatic alkyl substituted phenols; hydroxybenzoic acids; bisphenols, bis(hydroxyphenyl) alkanes, and hydroxyquinolines such as 8-hydroxyquinoline. Specific types of vapors and the amount thereof are selected with regard to the level of decontamination desired such as disinfection, sanitization, and the like. In other words, the apparatus and process of the present invention result in a microbial log reduction of generally at least about 3, desirably at least about 4, and preferably at least about 6. A log reduction of 6 means that one or less microorganisms in 1 million remain following exposure to the vapor. The antimicrobial vapors of the present invention are utilized to destroy various microorganisms including endospores, fungi, mycobacteria, vegetative bacteria, protozoa, and the like. The vapors utilized also deactivate or destroy other harmful microorganism-size biological species, and smaller replicating species, particularly those capable of undergoing conformational changes, such as prions. Of the various antimicrobial vapors which can be utilized, hydrogen peroxide is preferred since it is environmentally friendly, and in vapor form is generally materially compatible in that it does not adversely affect the various surfaces, items, fabrics, or materials which exist in the vehicle.

The antimicrobial compound whether it is obtained from a container or a generator 40 is generally subjected to a plurality of operations by preconditioning unit 41 before it is admitted to decontamination duct network 30. For example, as shown in FIG. 1, the antimicrobial compound is first fed to a dryer 42 to remove moisture and solvents, etc., therefrom, subsequently fed to blower 43 which forces the compound through preheater 45 and through a filter such as HEPA filter 47 to remove fine particles such as dust, etc., and the like. Finally, vaporizer 49 heats the antimicrobial compound to a temperature above its boiling point. Antimicrobial generator 40 and preconditioning unit 41 can be located in the vehicle as shown, or they can be located outside.

The antimicrobial vapor from preconditioning unit 41 is then fed to decontamination duct network 30 via entrance valve 31 which either blocks the entrance of any vapor into the duct system or permits the vapor to pass freely therethrough. Once valve 31 is opened, blower 43 will push the vapor through decontamination duct 30 whereupon it will travel along the length of the duct and be released to various outlets in patient area 12. If it is desired that the vapor be admitted to driver or cockpit area 14, two-way cockpit valve 32 is opened. Thus, the antimicrobial vapor will enter and permeate at least patient area 12 and decontaminate the various surfaces, items, instruments, and the like contained therein. If cockpit valve 32 is open, the vapor will also decontaminate the cockpit area but since an additional area is decontaminated, a decontamination cycle time will be longer.

In order to reduce the decontamination cycle time, auxiliary circulation duct network 50 is utilized. As shown in the drawing, auxiliary circulation duct 50 contains inlet valve 51 which allows ambient air to enter and through high capacity auxiliary blower 53 the air is fed through circulation network 50 and into patient area 12 and if circulation duct cockpit valve 55 is opened, also into cockpit area 14. The flow rate of air, or optionally but less desirable, a different gas, is much greater than that of the vapor through decontamination duct 30. Generally the ratio of the air through auxiliary circulation duct 50 to the antimicrobial vapor is generally from about 1 to about 20 or 50 times greater by volume. This high flow rate circulates and diffuses the antimicrobial vapor throughout the patient area and optionally the cockpit area and allows the vapor to enter or reach difficult areas.

In order to compensate for the additional air supplied to the vehicle, egress duct 60 allows the air and vapor to be recirculated throughout the vehicle or to be exhausted to the atmosphere outside of the vehicle, or both. Accordingly, egress duct 60 contains a filter such as a HEPA filter 62, recirculation valve 64, and catalytic converter 66. In a closed loop configuration, two-way valve 64 will allow the air and vapor to be recirculated through line 68 to preconditioning unit 41 which will draw the air and vapor and optionally additional liquid sterilant from generator 40, reheat and vaporize the same, and blow the same into decontamination duct 30. If essentially all of the recirculation air and vapor are recycled, auxiliary circulation duct 50 can be closed through inlet valve 51. Alternatively, a portion of the recirculation air and vapor is recycled with the remainder being fed to catalytic converter 66 which detoxifies the antimicrobial vapor before it is released to the Earth's atmosphere. Thus, when the vapor and recirculation air is partially recycled, the amount of additional recirculation air admitted through auxiliary circulation duct 50 is generally equal to that released through catalytic converter 66. In an open loop configuration wherein generally all of the air within the patient area and optionally the cockpit area is vented to the atmosphere through egress ducts 60, recirculation valve 64 is in the open position so the vapor is detoxified by catalytic converter 66.

The decontamination cycle is allowed to continue for a predetermined amount of time calculated to effectively destroy or deactivate the microorganisms thought or expected to be present. After such time, decontamination duct valve 31 is closed. If auxiliary circulation inlet valve 51 is open, it too is closed and auxiliary blower 52 turned off.

In order to purge the remaining antimicrobial vapor not utilized in deactivating or destroying the various microorganisms, aeration duct network 70 is utilized. As shown in FIG. 1, the aeration duct network has inlet valve 72 which admits air from outside of the vehicle and blower 74 forces the air through aeration duct network 70 to purge the antimicrobial vapor from patient area 12 of the vehicle, and if necessary through open cockpit valve 76 also from cockpit area 14. The purged vapor is forced through egress duct 60 through the filter, and since recycle valve 64 is closed, through catalytic converter 66 whereby it is detoxified. Catalytic converters are known to the art and to the literature and in the case of the antimicrobial vapor being hydrogen peroxide, the same is converted into water and oxygen. The aeration duct network is operated until the vapor level in the vehicle is determined to be below a safe level such as 1 part per million as measured with vaporous hydrogen peroxide, etc., with real time concentration sensors. Optionally, incoming aeration air can be heated to further optimize aeration of the antimicrobial vapor.

The above integrated duct system can be further modified to provide a quick, and efficient decontamination cycle as by utilizing various fans throughout the enclosed area(s) to efficiently diffuse the vapor into all areas, as well as through the utilization of materials which do not readily absorb microorganisms such as foam seat cushions, insulation, and the like.

Other aspects of the invention include the utilization of various devices to automate the various cycles such as the amount of antimicrobial vapor being admitted to the vehicle, the time and temperature of the decontamination cycle, the time of the auxiliary circulating cycle, the time and temperature of the aeration cycle, and the like. For example, a remote hydrogen peroxide sensor can exist within the vehicle to determine the concentration of the vapor which through an integrated feedback system is fed to a location or station outside the vehicle. Accordingly, an operator can control the vapor concentration either before or after circulating duct network 50 has been utilized, or both. Similarly, upon initiation of the aeration system the operator can determine from a safe location that the concentration of the vapor within the vehicle has dropped to a safe and low level. While in accordance with the patent statutes, the best mode and preferred embodiment have been set forth, the scope of the invention is not limited thereto, but rather by the scope of the attached claims.

What is claimed is:

1. A method of decontaminating a vehicle comprising the steps of:
   providing an interior portion of said vehicle with an integrated antimicrobial generator and an integrated duct system, for admitting and diffusing an antimicrobial vapor;
   providing said vehicle with a decontamination duct and admitting an antimicrobial vapor through said duct into said vehicle;
   providing said vehicle with an auxiliary circulation duct and admitting a gas through said circulation duct into said vehicle that contains said antimicrobial vapor;
   providing said vehicle with an aeration duct and exhausting said antimicrobial vapor and said gas to an egress duct provided within the interior of said vehicle;
   said decontamination duct, said auxiliary circulation duct, and said aeration duct each being located within the interior of said vehicle and each being separated from any remaining ducts; and
   said egress duct separately connected to a recirculation line and separately connected to a catalytic converter, and recirculating at least a portion of said gas and said antimicrobial vapor to said decontamination duct or exhausting at least a portion of said gas and said antimicrobial vapor to said catalytic converter for detoxifying said antimicrobial vapor or both.

2. A method according to claim 1, wherein said antimicrobial vapor is a peroxy compound, an aldehyde, or a phenol or a derivative thereof.

3. A method according to claim 2, wherein said vapor is hydrogen peroxide, wherein said gas admitted to said circulation duct is air, and including an auxiliary blower for feeding said air into said circulation duct, and including an aeration blower for feeding air into said aeration duct.

4. A method according to claim 3, wherein said antimicrobial generator is a hydrogen peroxide generator, and including a heating duct for admitting heated air into said vehicle.

5. A method according to claim 1, wherein said vapor achieves a decontamination log reduction of at least 3.

6. A method according to claim 3, wherein said vapor achieves a decontamination log reduction of at least 4.

7. A method according to claim 4, wherein said vapor achieves a decontamination log reduction of at least 6.

* * * * *